(12) United States Patent
Kim et al.

(10) Patent No.: US 7,482,027 B2
(45) Date of Patent: Jan. 27, 2009

(54) COMPOSITION FOR THE PREVENTION OR TREATMENT OF DISEASES ASSOCIATED WITH ANGIOGENESIS

(75) Inventors: Min-Young Kim, Daejeon (KR); Hyun-Ok Yang, Seoul (KR); Jaewan Choi, Seoul (KR)

(73) Assignee: AngioLab, Inc., Yuseong-gu, Daejeon (KR)

( * ) Notice: Subject to any disclaimer, the term of this patent is extended or adjusted under 35 U.S.C. 154(b) by 16 days.

(21) Appl. No.: 11/118,714

(22) Filed: Apr. 30, 2005

(65) Prior Publication Data

US 2006/0246157 A1 Nov. 2, 2006

(51) Int. Cl.
*A01N 65/00* (2006.01)

(52) U.S. Cl. .................................................... 424/725

(58) Field of Classification Search ................ None
See application file for complete search history.

(56) References Cited

FOREIGN PATENT DOCUMENTS

| KR | 2002023456 | * | 3/2002 |
| KR | 10-547366 | | 1/2006 |

OTHER PUBLICATIONS

Kwak et al., Anti-angiogenic activities of Cnidium officinale Makino and *Tabanus bovinus*, Journal of Ethnopharmacology, 81: 373-379, 2002.*
Kobayashi et al (Chem Pharm Bull 35(4): 1427-1433, 1987).*
O'Day (Int Ophthalmol Clin., 36(2): 45-51, 1996).*
Kamb, What's wrong with our cancer models? Nature Reviews, 4: 161-165, 2005.*
Folkman J and Cotran R, Int. Rev. Exp. Pathol., 16 207-248 (1976) "Relation of vascular proliferation to tumor growth".
D'Amato RJ and Adamis AP, Ophthalmol., 102 1261-1262 (1995) "Angiogenesis inhibition in age-related macular degeneration".
Arbiser JL, J. Am. Acad. Derm., 34(3) 486-497 (1996) "Angiogenesis and the skin: a primer".
O'Brien KD, McDonald TO, et al., Circulation, 93(4) 672-682 (1996) "Neovascular expression of E-selectin, intercellular adhesion molecule-1~".
Hanahan D and Folkman J, Cell, 86 353-364 (1996) "Patterns and emerging mechanisms of the angiogenic switch during tumorigenesis".
Polverini PJ, Critical Reviews in Oral Biology, 6(3) 230-247 (1995) "The pathophysiology of angiogenesis".
Koch AE, Polverini PJ et al., Arth. Rheum., 29 471-479 (1986) "Stimulation of neovascularization by human rheumatoid synovial tissue macrophages".
Stupack DG, Storgard CM, et al., Braz. J. Med. Biol. Rcs., 32 578-581 (1999) "A role for angiogenesis in rheumatoid arthritis".
Koch AE, Arth. Rheum., 41 951-962 (1998) "Angiogenesis: implications for rheumatoid arthritis".
Isner JM and Asahara T, J. Clin. Invest., 103(9) 1231-1236 (1999) "Angiogenesis and vasculogenesis as therapeutic strategies for postnatal neovascularization".
Folkman J., J. Invest. Dermatol., 59 40-48 (1972) "Angiogenesis in psoriasis: therapeutic implications".
Rupnick MA, Panigrahy D, et al., Proc. Natl. Acad. Sci. U.S.A., 90(16) 10730-10735 (2002) "Adipose tissue mass can be regulated through the vasculature".
Vagnucci AH and Li WW, Lancet, 361(9357) 605-608 (2003) "Alzheimer's disease and angiogenesis".
Kobayashi M, Fujita M et al. Chem. Pharm. Bull., 35(4) 1427-1433 (1987) "Studies on the constituents of Umbelliferae plants. XV. Constituents ~".
Harborne JB Phytochemical methods: A guide to modern techniques of plant analysis. 3rd Ed., pp. 6-7, 1998.
Kenyon BM, Voest EE, et al., .Invest. Ophthalmol Vis. Sci., 37 1625-1632 (1996) "A model of angiogenesis in the mouse cornea".
Li WW, Grayson G, et al., Invest. Ophthalmol Vis. Sci., 32 2906-2911 (1991) "Sustained-release endotoxin. A model for inducing corneal neovascularization".

* cited by examiner

*Primary Examiner*—Michael V Meller
*Assistant Examiner*—Qiuwen Mi
(74) *Attorney, Agent, or Firm*—Joseph Hyosuk Kim; JHK Law

(57) ABSTRACT

The present invention relates to a composition for the prevention or treatment of diseases associated with angiogenesis, and in detail, to a composition comprising the extract of *Cnidium officinale* Makino or the fraction thereof for the prevention or treatment of diseases associated with angiogenesis. The present invention also provides 3-butyl-7-hydroxyphthalide, vanillin, coniferyl ferulate, and falcarindiol as active compounds. The composition of the present invention inhibits angiogenesis, so that it can be applied to the prevention or treatment of diseases related to angiogenesis, such as arthritis, diabetic retinopathy, psoriasis, and cancer.

4 Claims, 6 Drawing Sheets

Corneal Neovascularization Score

COMPOSITION FOR THE PREVENTION OR TREATMENT OF DISEASES ASSOCIATED WITH ANGIOGENESIS

FIELD OF INVENTION

The present invention relates to a composition comprising the extract of *Cnidium officinale* Makino or the fraction thereof for the prevention or treatment of diseases associated with angiogenesis. The composition of the present invention inhibits angiogenesis, so that it can be applied to the prevention or treatment of diseases related to angiogenesis, such as arthritis, diabetic retinopathy, psoriasis, and cancer.

BACKGROUND OF THE INVENTION

The present invention relates to a composition for the prevention or treatment of diseases associated with angiogenesis, and in detail, to a composition comprising the extract of *Cnidium officinale* Makino (*C. officinale*) or the fraction thereof for the prevention or treatment of diseases associated with angiogenesis.

Angiogenesis is the process of generating new capillary blood vessels. Neovascularization is tightly regulated, and its activation occurs in embryogenic development, tissue remodeling, wound healing, and periodic cycles of corpus luteum development (Folkman and Cortran, *Int. Rev. Exp. Pathol.*, 16, pp 207-248, 1976).

For the case of adult, the endothelial cells very slowly proliferate and rarely differentiate as compared with other types of cells in the body.

In general, the process of angiogenesis consists of proteolytic degradation of endothelial basement membrane induced by angiogenic factors; movement and proliferation of endothelial cells; tube formation induced by differentiation of endothelial cells; rearrangement of blood vessels; and formation of new capillary blood vessels.

Some diseases are developed by the failure of regulation of angiogenesis and the pathological growth of blood vessels. Cardiovascular diseases such as angioma, angiofibrioma, vascular deformity, atherosclerosis, synechia and edemic sclerosis; and ophthalmologic diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are diseases related to angiogenesis. Chronic inflammatory diseases such as arthritis; dermatological disease such as psoriasis, telangiectasis, pyogenic granuloma, seborrheic dermatitis and acne; and Alzheimer's disease, obesity, and the growth and metastasis of cancer are also angiogenesis-dependent diseases (D'Amato R J and Adamis A P, *Ophthalmol.*, 102, pp 1261-1262, 1995; Arbiser J L. *J. Am. Acad. Derm.*, 34(3), pp 486-497, 1996; O'Brien K D et al. *Circulation*, 93(4), pp 672-682, 1996; Hanahan D and Folkman J, *Cell*, 86, pp 353-364, 1996).

In particular, angiogenesis is essential to growth and metastasis of cancer. New blood vessels not only provide nutrients and oxygen to fast-growing cancer cells, but also give ways of entering the blood stream resulting in metastasis (Folkman and Tyler, *Cancer Invasion and Metastasis*, Biological mechanisms and Theraphy (S. B. Day ed.) Raven press, New York, pp 94-103, 1977; Polverini P J, *Critical Reviews in Oral Biology*, 6(3), pp 230-247, 1995). Currently, a large variety of chemotherapies and immunotherapies are applied in the treatment of cancer, but the efficacy of these therapies is limited and nothing can successfully extend the life of cancer patients due to the lack of anti-metastasis effects.

Arthritis, a well-known inflammatory disease, is initiated as an autoimmune disease. During the progression of inflammation, the growth of vascular endothelial cell in synovial cavity is activated by cytokines. The cartilage in articulation is finally destroyed by the formation of articular lamina leak (Kocb A E et al., *Arth. Rheum.*, 29, pp 471-479, 1986; Stupack D G et al., *Braz. J. Med. Biol. Rcs.*, 32, pp 578-581, 1999; Koch A E, *Arth. Rheum.*, 41, pp 951-962, 1998).

Many people are losing their eyesight all over the world because of various ocular diseases. Many patients became blind due to the infiltration of capillary blood cells into the vitreous humor (Jeffrey M I and Takayuki A, *J. Clin. Invest.*, 103, pp 1231-1236, 1999). Therefore, the inhibition of angiogenesis is the basic therapeutic modality for these diseases.

Psoriasis is caused by extremely active proliferation of skin cells. Fast-growing cells require sufficient blood supply, and angiogenesis is abnormally induced in psoriasis (Folkman J., *J. Invest. Dermatol.*, 59, pp 40-48, 1972).

For the case of obesity, adipose tissue mass can be regulated by its vasculature, and the treatment of angiogenesis inhibiter decreases both body weight and adipose tissue mass in dose-dependent manner (Rupnick M A et al., *Proc. Natl. Acad. Sci. U.S.A.*, 90(16), pp 10730-10735, 2002).

In Alzheimer's diseases, it was found that large populations of endothelial cells are activated by angiogenesis due to brain hypoxia and inflammation, and the brain endothelium secretes the precursor substrate for beta-amyloid plaque and a neurotoxin peptide. Alzheimer's disease can be treated and prevented by angiogenesis inhibitors, which are specific to abnormal brain endothelial cells (Vagnucci A H et al., *Lancet*, 361, pp 605-608, 2003).

Since angiogenesis is closely related to initiation and progression of many diseases, many efforts have been made toward the development of angiogenesis inhibitors in order to prevent or treat these diseases. Since these inhibitors need to be administered for a long time, desirable inhibitors should not have toxic or adverse effects with good patient compliance.

*C. officinale* is a plant in Umbelliferae. In folk medicine, its dried root has been used for headache, infertility, menstrual disorder, anemia, and tonic. Chemical compositions of *C. officinale* consist of phthalide compounds such as cnidilide, neocnidilide, ligustilide, butylphthalide, and senkyunolide (Fuzita M. and Kobayashi M., *Chem. Pharm. Bull.*, 35(4), pp 1427-1433, 1987).

The present inventors have found that the extracts of *C. officinale* and the fractions thereof have inhibitory effects on angiogenesis, and they have purified effective ingredients from extracts of *C. officinale* that can inhibit angiogenesis.

SUMMARY OF THE INVENTION

The present invention is directed to an extract of *C. officinale* and a fraction thereof that inhibits angiogenesis. Also, the inventors have identified 3-butyl-7-hydroxyphthalide, vanillin, coniferyl ferulate, and falcarindiol as active ingredients and they may be used alone or in any combination with one another, such as 3-butyl-7-hydroxyphthalide and vanillin; 3-butyl-7-hydroxyphthalide and coniferyl ferulate or its angiogenesis inhibiting derivative thereof; 3-butyl-7-hydroxyphthalide and falcarindiol; 3-butyl-7-hydroxyphthalide, vanillin and coniferyl ferulate or its angiogenesis inhibiting derivative thereof; 3-butyl-7-hydroxyphthalide, vanillin and falcarindiol; 3-butyl-7-hydroxyphthalide, vanillin, coniferyl ferulate or its angiogenesis inhibiting derivative thereof, and falcarindiol; vanillin and coniferyl ferulate or its angiogenesis inhibiting derivative thereof; vanillin and falcarindiol; vanillin, coniferyl ferulate or its angiogenesis inhibiting derivative thereof, and falcarindiol; or coniferyl ferulate or its angiogenesis inhibiting derivative thereof and falcarindiol.

Accordingly, the present invention provides an anti-angiogenic composition comprising an extract of *C. officinale* and a fraction thereof as active ingredient. More specifically, the present invention provides an anti-angiogenic composition for pharmaceutical or nutraceutical use. Thus, the composition of the present invention can be used for the treatment or prevention of diseases derived from angiogenesis.

The invention is directed to a composition comprising an extract of *Cnidium officinale* Makino for the prevention or treatment of angiogenesis-related diseases. In particular, the extract is prepared using a solvent selected from a group consisting of water, C1-C4 lower alcohol, and their mixture. The invention is also directed to a composition comprising non-polar solvent extract of *Cnidium officinale* Makino or a fraction thereof for the prevention or treatment of angiogenesis-related diseases, in particular, the extract is prepared using a solvent selected from a group consisting of hexane, chloroform, methylene chloride, and ethyl acetate and further in particular, the extract is prepared using chloroform. In certain respects, the present invention is directed to the composition comprising non-polar solvent extract of *Cnidium officinale* Makino or a fraction thereof comprising 3-butyl-7-hydroxyphthalide, falcarindiol, vanillin, or coniferyl ferulate or a derivative thereof having anti-angiogenic activity. In another aspect, the invention is directed to the composition comprising non-polar solvent extract of *Cnidium officinale* Makino or a fraction thereof, including any of the following alone or in any combination: 3-butyl-7-hydroxyphthalide, falcarindiol, vanillin and coniferyl ferulate.

The invention is further directed to a method of making the composition comprising non-polar solvent extract of *Cnidium officinale* Makino or a fraction thereof for the prevention or treatment of angiogenesis-related diseases comprising:

i) obtaining 4 fractions from chloroform extract of *Cnidium officinale* Makino using silica gel chromatography with chloroform:methanol (20:1) mixture as developing solvent in the flow rate of 100 ml per hour;

ii) obtaining another 5 fractions from the second fraction of the above fractionation using silica gel chromatography with ethylacetate:hexane (1:6) mixture as developing solvent;

iii) obtaining 4 fractions from the third fraction of the second fractionation using silica gel chromatography with ethylacetate:hexane (1:20) mixture as developing solvent;

iv) obtaining 4 fractions from the second fraction of the third fractionation using reversed phase HPLC with methanol:water (60:40) at a flow rate of 1.5 ml; and v) providing the third fraction of final fractionation as active ingredient for inhibition of angiogenesis.

Furthermore, the present invention is also directed to a method of making the composition comprising non-polar solvent extract of *Cnidium officinale* Makino or a fraction thereof for the prevention or treatment of angiogenesis-related diseases comprising:

i) obtaining 4 fractions from chloroform extract of *Cnidium officinale* Makino using silica gel chromatography with chloroform:methanol (20:1) mixture as developing solvent in the flow rate of 100 ml per hour;

ii) obtaining another 5 fractions from the second fraction of the above fractionation using silica gel chromatography with ethylacetate:hexane (1:6) mixture as developing solvent;

iii) obtaining 3 fractions from the fourth fraction of the second fractionation using silica gel chromatography with ethylacetate:hexane (1:20) mixture as developing solvent;

iv) obtaining 5 fractions from the second fraction of the third fractionation using reversed phase HPLC with methanol:water (70:30) at a flow rate of 0.8 ml; and v) providing the fourth fraction of final fractionation as active ingredient for inhibition of angiogenesis.

In certain aspects, the present invention is directed to a method of reducing angiogenesis in a subject comprising administering the composition comprising an extract of *Cnidium officinale* Makino for the prevention or treatment of angiogenesis-related diseases to a subject in need thereof.

In another aspect of the invention, the invention is directed to a method of treating angiogenesis-related disease in a subject comprising administering the composition comprising an extract of *Cnidium officinale* Makino for the prevention or treatment of angiogenesis-related diseases to a subject in need thereof, in particular, the angiogenesis-related disease may be angioma, angiofibrioma, vascular deformity, atherosclerosis, synechia, edemic sclerosis, ophthalmologic diseases, chronic inflammatory diseases, dermatological diseases, Alzheimer's disease, obesity, or cancer and still in particular. The ophthalmologic disease may be neovascularization after cornea implantation, neovascular glaucoma, diabetic retinopathy, angiogenic corneal disease, macular degeneration, pterygium, retinal degeneration, retolental fibroplasias, or granular. The chronic inflammatory disease may be arthritis and the dermatological disease may be psoriasis, telangiectasis, pyogenic granuloma, seborrheic dermatitis or acne.

The invention is further directed to a nutraceutical composition comprising an extract of *Cnidium officinale* Makino and food additive for the prevention or enhancement for angiogenesis-related diseases, in particular, the extract may be prepared using a solvent selected from a group consisting of water, C1-C4 lower alcohol, and their mixture, and further in particular, the extract may be prepared using chloroform.

The invention is also directed to a nutraceutical composition comprising non-polar solvent extract of *Cnidium officinale* Makino or a fraction thereof and permissible food additive for the prevention or treatment for angiogenesis-related diseases.

These and other objects of the invention will be more fully understood from the following description of the invention, the referenced drawings attached hereto and the claims appended hereto.

DETAILED DESCRIPTION OF THE INVENTION

Figure 1:
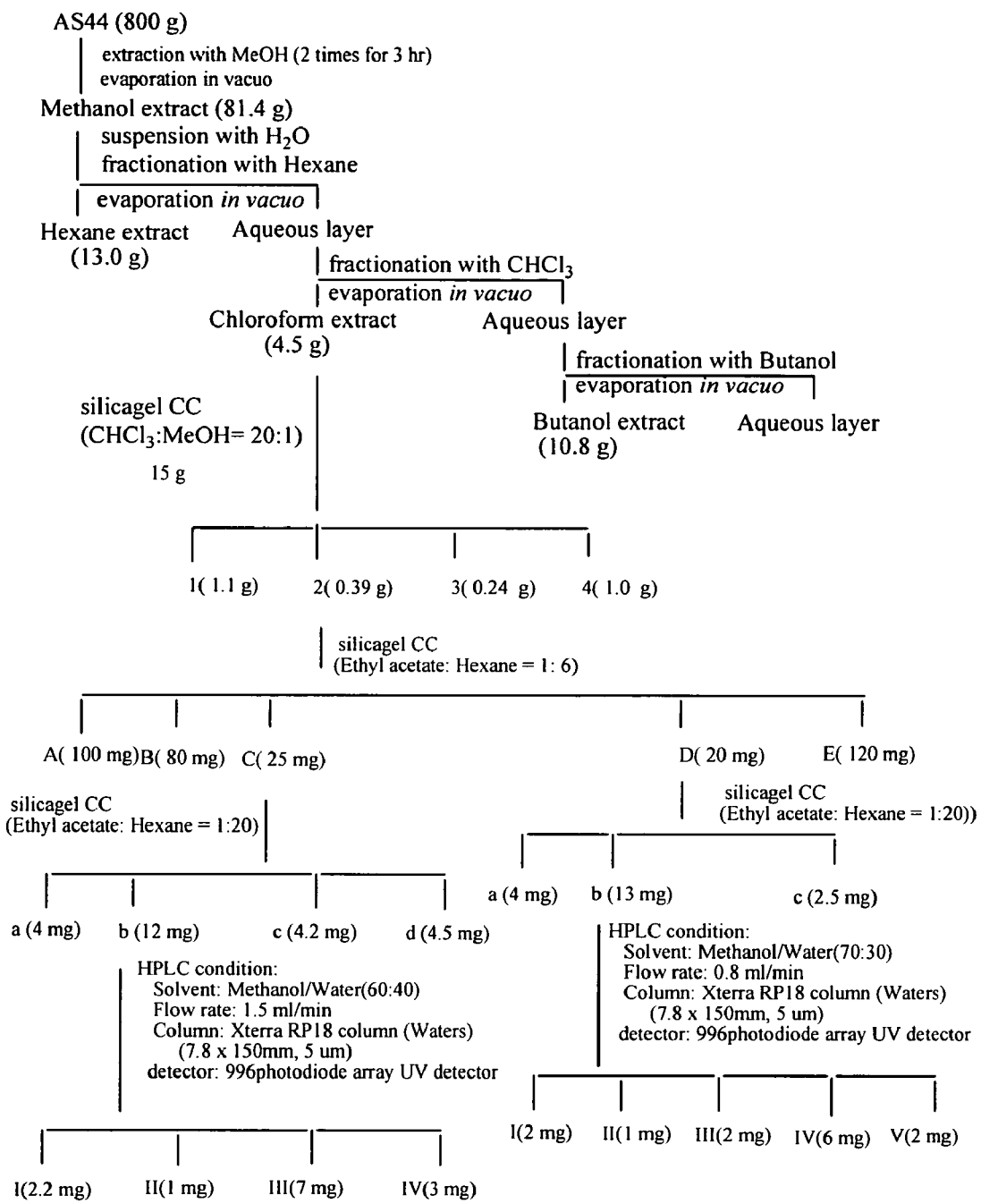
FIG. 1 is a picture showing the method for extraction and fractionation of *C. officinale*.

Accordingly, it is an object of the present invention to provide an anti-angiogenic composition comprising crude extract of *C. officinale* for the treatment or prevention of angiogenesis-related diseases.

The above crude extract includes an extract prepared using a solvent such as water, C1-C4 lower alcohol, and their mixture, desirably, water and ethanol.

Also, it is another object of the present invention to provide an anti-angiogenic composition comprising non-polar solvent extract of *C. officinale* or the fraction thereof for the treatment or prevention of angiogenesis-related diseases.

The above non-polar solvent extract includes an extract prepared using a non-polar solvent such as hexane, chloroform, methylenechloride, and ethylacetate, desirably, chloroform.

The fraction mentioned above includes the fraction obtained from chloroform extract of *C. officinale* using silica gel column chromatography with chloroform:methanol or ethylaectate:hexane mixture as developing solvent.

In addition, the present invention provides fraction of *C. officinale* obtained by the following method. 4 fractions (AS44-C-1, -2, -3, -4) are obtained from chloroform extract of *C. officinale* using silica gel chromatography with chloroform:methanol (20:1) mixture as developing solvent at the flow rate of 100 ml per hour. 5 fractions (AS44-C-2-A, -B, -C, -D, -E) are obtained from AS44-C-2 using silica gel chromatography with ethylacetate:hexane (1:6) mixture as developing solvent. 4 fractions (AS44-C-2-C-a, -b, -c, -d) and 3 fractions (AS44-C-2-D-a, -b, -c) are obtained from AS44-C-2-C and AS44-C-2-D using silica gel chromatography with ethylacetate:hexane (1:20) mixture as developing solvent, respectively. 4 fractions (AS44-C-2-C-b-I, -II, -III, -IV) are finally obtained from AS44-C-2-C-b using HPLC (Waters) equipped with Waters 996 photodiode array UV detector. A semi-preparative reversed phase column (Waters Xterra C18, 5 μm, 150×7.8 mm) was used for separations with methanol:water (60:40) at a flow rate of 1.5 ml/min. Also, 5 fractions (AS44-C-2-D-b-I, -II, -III, -IV, -V) are obtained from AS44-C-2-D-b using the same HPLC condition as mentioned above with methanol:water (70:30) at a flow rate of 0.8 ml/min. AS44-C-2-C-b-III and AS44-C-2-D-b-IV which are identified as 3-butyl-7-hydroxyphthalide and falcarindiol (1,9-decadiene-4,6-diyne-3,8-diol), respectively, or a combination thereof are provided as active compounds.

The inventive crude extract of *C. officinale* prepared by polar solvent can be obtained by extraction of the powder of dried roots, leaves, and stems of *C. officinale* with 1 to 20 parts, desirably 3 to 10 parts of water, C1-C4 lower alcohol, or their mixture, desirably water or ethanol at 20 to 100° C., desirably 50 to 100° C. for 1 hour to 10 days, desirably 2 to 5 hours using conventional extraction method such as cold extraction, heat extraction, microwave extraction, and reflux cooling extraction following filtration, concentration, and drying.

Also, non-polar solvent extract of the present invention can be obtained by extraction of aqueous suspension of the above polar solvent crude extract with 1 to 100 parts, desirably 1 to 5 parts of non-polar solvent such as hexane, chloroform, methylenechloride, and ethylacetate, desirably chloroform 1 to 10 times, desirably 2 to 5 times. Also, non-polar solvent extract of the present invention can be further prepared by additional fractionation using conventional method (Harborne J B, Phytochemical methods: *A guide to modern techniques of plant analysis.* $3^{rd}$ Ed., pp 6-7, 1998).

For desirable example, the fraction of *C. officinale* provided by the present invention is obtained by extraction of *C. officinale* with organic solvent. In detail, methanol extract (AS44-M) is obtained by extraction of dried *C. officinale* with methanol, and then hexane extract (AS44-H), chloroform extract (AS44-C), butanol extract (AS44-B), and aqueous extract (AS44-W) are obtained by the fractionation of AS44-M. 4 fraction (AS44-C-1, -2, -3, -4) are obtained from chloroform extract (AS44-C), which has inhibitory effects on angiogenesis, using silica gel column chromatography with chloroform:methanol solvent, desirably 15:1 to 25:1 volume ratio of chloroform:methanol solvent. The effective fraction AS44-C-2 is applied to silica gel chromatography with ethylacetata:hexane solvent, desirably 1:1 to 1:5 volume ratio of ethylacetate:hexane solvent, and then 5 fractions (AS44-C-2-A, -B, -C, -D, -E) are obtained. Repeatedly, the effective fraction AS44-C-2-C is applied to silica gel chromatography with ethylacetata:hexane solvent, desirably 1:1 to 1:5 volume ratio of ethylacetate:hexane solvent, and then 4 fraction (AS44-C-2-C-a, -b, -c, -d) are obtained. The effective fraction AS44-C-2-C-b is applied to HPLC (Waters) and then 4 fractions (AS44-C-2-C-b-I, -II, -III, -IV) are obtained.

Also, another effective fraction AS44-C-2-D is applied to silica gel chromatography with ethylacetate:hexane solvent, desirably 1:1 to 1:5 volume ratio of ethylacetate:hexane solvent, and then 3 fraction (AS44-C-2-D-a, -b, -c) are obtained. The effective fraction AS44-C-2-D-b is applied to HPLC (Waters) and then 5 fractions (AS44-C-2-D-b-I, -II, -III, -IV, -V) are obtained.

Inhibitory effects of active fractions of the present invention on angiogenesis were confirmed by various methods in examples provided in the present invention. Because anti-angiogenic properties of aqueous crude extract and chloroform extract of *C. officinale* and the fraction thereof (AS44-C, AS44-C-2, AS44-C-2-C, and AS44-C-2-C-b, AS44-C-2-C-b-III, AS44-C-2-D, AS44-C-2-D-b, AS44-C-2-D-b-IV) showed inhibitory effects on HUVEC tube formation, HUVEC proliferation, and angiogenesis of animal model (mouse Matrigel model and corneal neovascularization), these extracts and fractions may be effective on the treatment or prevention of angiogenesis-related diseases. Two active compounds, AS44-C-2-C-b-III and AS44-C-2-D-b-IV were identified as 3-butyl-7-hydroxyphthalide and falcarindiol by NMR spectroscopy. Other active compounds in AS44-C-2 fraction include the following compounds:

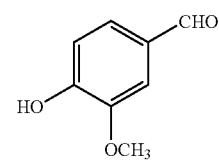

Vanillin (4-hydroxy-3-methoxybenzaldehyde) and

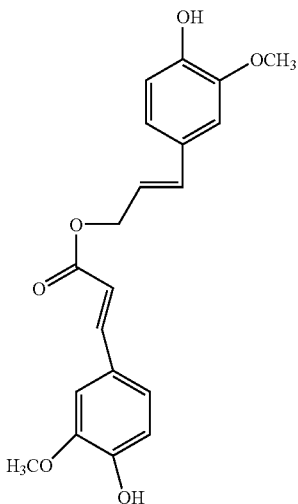

Coniferyl ferulate (3-(4-hydroxy-3-methoxyphenyl)-2-propenyl ester). It is believed that these chemical compounds, alone or in combination are active ingredients for anti-angiogenic activity of the active AS44-C-2. Further, a derivative of coniferyl ferulate having the function of inhibiting angiogenesis is included in the invention.

The present invention provides a composition comprising anti-angiogenic extract of *C. officinale* or the fraction thereof as active ingredient for the treatment or prevention of angiogenesis-related diseases.

The pharmaceutical or preventive composition of the present invention can be used to prevent or treat angiogenesis-related diseases, such as angioma, angiofibrioma, vascular deformity, atherosclerosis, synechia and edemic sclerosis; ophthalmologic diseases such as neovascularization after cornea implantation, neovascular glaucoma, diabetic retinopathy, angiogenic corneal disease, macular degeneration, pterygium, retinal degeneration, retolental fibroplasias, and granular; chronic inflammatory diseases such as arthritis; dermatological disease such as psoriasis, telangiectasis, pyogenic granuloma, seborrheic dermatitis and acne; and Alzheimer's disease, obesity, cancer, and so on, but it is not limited.

The inventive composition can be used to treat angiogenesis-related growth and metastasis of cancer, such as lung cancer, non-small cell lung cancer, liver cancer, colon carcinoma, bone cancer, pancreas cancer, skin cancer, head and neck cancer, skin and ocular melanoma, uterine carcinoma, ovarian cancer, rectal cancer, stomach cancer, anal cancer, breast cancer, carcinoma of the fallopian tube, endometrial cancer, cervical cancer, vaginal cancer, vulva cancer, Hodgkin's disease, esophageal cancer, small intestine tumor, endocrine carcinoma, thyroid cancer, parathyroid cancer, adrenal tumor, soft tissue sarcoma, urethra tumor, penis cancer, bladder cancer, kidney and ureter cancer, renal cell carcinoma, CNS tumor, primary CNS lymphoma, spinal cord tumor, brain stem glioma, pituitary adenoma, and so on.

The composition of the present invention could contain 0.01 to 99.9% (w/w), desirably 0.1 to 90% (w/w) of extract of *C. officinale* or fraction thereof. But it is not limited, and the composition can be changed according to the severity of patient's symptoms, age, sex, body weight of the individual patient, dosing time, and the chosen route of administration.

The composition of the present invention can be administered orally and non-orally for the clinical administration, and it can be used in the form of conventional formulation.

That is, the composition of the present invention comprising extract of *C. officinale* or fraction thereof can be administered orally or non-orally for the clinical administration in the various form of formulation, which can be consisted of diluent or vehicle, such as filler, diluent, binding agent, wetting agent, disintegrant, and surfactant.

The composition of the present invention comprising extract of *C. officinale* or fraction thereof can be used in any form, such as oral dosage form (powder, granule, tablet, pill, capsule, suspension, emulsion, syrup, aerosol), topical preparation, suppository, or sterile injection.

The solid formulation may include more than one of vehicle, such as dextrin, starch, calcium carbonate, sucrose, lactose, gelatin and so on. Also, lubricant such as magnesium stearate and talc may be used in addition to simple vehicle. Oral liquid formulation such as suspension, emulsion, syrup, and so on, may include diluent such as water and liquid paraffin; and also include some vehicles such as wetting agent, sweetening agent, aromatic, preserving agent, and so on. Non-oral formulation includes sterile aqueous solution, non-polar solution, suspension, emulsion, freezing dried agent, and suppository. Propylene glycol, polyethylene glycol, vegetable oil such as olive oil, injectable ester such as ethyl oleate, and so on may be used for non-polar solution and suspension. Suppository base may be consisted of witepsol, macrogol, tween 61, Oleaum Cacao, Sevum Laurinum, glycerogelatin, and so on.

Desirable dose of extracts or fractions provided by the present invention may be altered according to the severity of patient's symptoms, age, sex, body weight of the individual patient, dosing time, and the chosen route of administration. In general, the dose of formulation of the present invention should contain 0.01 mg/kg to 10 g/kg a day, desirably 1 mg/kg to 1 g/kg a day. The formulation may be administered in a single dose per day, or 2-3 divided doses per day.

The composition of the present invention may be administered to mammals such as rat, mouse, livestock, and human via various routes such as oral, transdermal, subcutaneous, intravenous, intraperitoneal, intramuscular, intra-arterial, intracerebroventricular, rectal, nasal, ocular, and topical introduction.

The present invention provides a nutraceutical composition comprising crude extract of *C. officinale* and permissible food additive for the prevention, improvement, or mitigation of angiogenesis-related diseases.

Also, the present invention provides a nutraceutical composition comprising non-polar solvent extract of *C. officinale* or the fraction thereof and food additive for the prevention, improvement, or mitigation of angiogenesis-related diseases.

The extract of *C. officinale* can be added into food, beverage, gum, tea, vitamin complex, nutraceutical, and so on.

Also, the extract of *C. officinale* can be added into food or beverage for the prevention, improvement, or mitigation of angiogenesis-related diseases. The content of extract mentioned above in food or beverage may be 0.01 to 90% (w/w) of total food weight, desirably 0.1 to 80% (w/w) for nutraceutical food composition, and 0.01 to 90 g per 100 ml, desirably 0.1 to 50 g for nutraceutical beverage composition.

The nutraceutical beverage composition of the present invention is not limited except that it contains the extract mentioned above as active ingredient, and can include several additives such as flavor or natural carbohydrate. Natural carbohydrates include monosaccharide such as glucose, fructose, and so on; disaccharide such as maltose, sucrose, and so on; polysaccharide such as common sugar (dextrin, cyclodextrin) and sugar-alcohol (xylitol, sorbitol, erythritol). Natural flavor (thaumatin, stevia extract such as rebaudioside A and glycyrrhizin) and artificial flavor (saccharin, arpartame) can be used as flavor mentioned above. The content of natural carbohydrate may be 1 to 20 g, desirably 5 to 12 g per 100 ml of composition provided by the present invention.

Except for the components mentioned above, the nutraceutical composition of the present invention can include nutrition, vitamin, mineral, flavor, coloring food additive, pectic acid and its salt, alginic acid and its salt, organic acid, protective colloid thickener, pH buffer, stabilizer, antiseptic, glycerin, alcohol, and so on. Also, the nutraceutical composition of the present invention can include flesh of fruit in order to manufacture natural fruit juice, fruit juice beverage, and vegetable beverage. These components can be used independently or in the form of mixture. The content of these additives are not important, but is generally 0 to 20% (w/w) of total weight of nutraceutical composition.

Hereinafter, the present invention will be explained in detail.

The following examples are intended to further illustrate the present invention. However, these examples are shown only for better understanding the present invention without limiting its scope.

EXAMPLE 1

Preparation of Crude Extract of *C. officinale* I 200 g of dried *C. officinal* was soaked in 1 liter of water, and then was extracted at 90 to 100° C. for 6 hours two times. The filtrate was evaporated in vacuo. Finally, 56.6 g of extract (AS44-TW) from *C. officinale* was obtained.

EXAMPLE 2

Preparation of Crude Extract of *C. officinale* II 800 g of dried *C. officinal* was soaked in 6 liters of 80% methanol, and then was extracted for 3 hours two times using reflux cooling system. The filtrate was evaporated in vacuo. Finally, 81.4 g of extract (AS44-M) from *C. officinale* was obtained.

EXAMPLE 3

Preparation of Non-Polar Solvent Extract of *C. officinale*

3-1. Preparation of Hexane Extract of *C. officinale*

81.4 g of methanol extract of *C. officinale* of the above EXAMPLE 2 was suspended in 1 liter of distilled water, and 200 ml of n-hexane was added. The mixture was vigorously mixed and it leaved alone until its layers were separated. Hexane extraction was done 3 times, and then hexane extract was evaporated in vacuo. Finally, 13 g of hexane extract (AS44-H) was obtained.

3-2. Preparation of Chloroform Extract of *C. officinale*

200 ml of chloroform was added into aqueous layer of the above EXAMPLE 3-1. The mixture was vigorously mixed and it leaved alone until its layers were separated. Chloroform extraction was done 3 times, and then chloroform extract was evaporated in vacuo. Finally, 4.5 g of chloroform extract (AS44-C) was obtained.

3-3. Preparation of Butanol and Aqueous Extract of *C. officinale*

200 ml of butanol was added into aqueous layer of the above EXAMPLE 3-2. The mixture was vigorously mixed and it leaved alone until its layers were separated. Butanol extraction was done 3 times, and then butanol extract was evaporated in vacuo. Finally, 10.8 g of butanol extract (AS44-B) was obtained.

The remaining aqueous layer was dried using freezing drying method, and 53.1 g of aqueous fraction was obtained.

EXAMPLE 4

Purification of Active Ingredients from Extract of *C. officinale*

4.5 g of chloroform extract (AS44-C) of *C. officinale* of the above EXAMPLE 3-2 was adsorbed to the same mass of silica gel, and then was applied to silica gel chromatography (7×70 cm, Merck). Chloroform:methanol (20:1, v/v) was used as developing solvent, and the flow rate was 100 ml per hour. Finally, 4 fractions (AS44-C-1, 1.11 g; AS44-C-2, 0.39 g; AS44-C-3, 0.24 g; AS44-C-4, 1.0 g) were obtained.

The active fraction, AS44-C-2 was applied to silica gel chromatography using ethyl acetate:hexane (1:6, v/v) as developing solvent. Finally, 5 fractions (AS44-C-2-A, 100 mg; AS44-C-2-B, 80 mg; AS44-C-2-C, 25 mg; AS44-C-2-D, 20 mg; AS44-C-2-E, 120 mg) were obtained.

The active fraction, AS44-C-2-C was applied to silica gel chromatography using ethyl acetate:hexane (1:20, v/v) as developing solvent, and 4 fractions (AS44-C-2-C-a, 4 mg; AS44-C-2-C-b, 12 mg; AS44-C-2-C-c, 4.2 mg; AS44-C-2-C-d, 4.5 mg) were obtained.

The active fraction, AS44-C-2-C-b was applied to HPLC (Waters) equipped with Waters 996 photodiode array UV detector. A semi-preparative reversed phase column (Waters Xterra C18, 5 µm, 150×7.8 mm) was used for separations with methanol:water (60:40) at a flow rate of 1.5 ml/min, and 4 fractions (AS44-C-2-C-b-I, 2.2 mg; AS44-C-2-C-b-II, 1 mg; AS44-C-2-C-b-III, $\partial$mg; AS44-C-2-C-b-IV, 3 mg) were obtained.

Also, the another active fraction, AS44-C-2-D was applied to silica gel chromatography using ethyl acetate:hexane (1:20, v/v) as developing solvent, and 3 fractions (AS44-C-2-D-a, 4 mg; AS44-C-2-D-b, 13 mg; AS44-C-2-D-c, 2.5 mg) were obtained.

The active fraction, AS44-C-2-D-b was applied to HPLC (Waters) equipped with Waters 996 photodiode array UV detector. A semi-preparative reversed phase column (Waters Xterra C18, 5 µm, 150×7.8 mm) was used for separations with methanol:water (70:30) at a flow rate of 0.8 ml/min, and 4 fractions (AS44-C-2-D-b-I, 2 mg; AS44-C-2-D-b-II, 1 mg; AS44-C-2-D-b-III, 2 mg; AS44-C-2-D-b-IV, 6 mg; AS44-C-2-D-b-V, 2 mg) were obtained.

10 mg/ml of extracts of *C. officinale* and fractions thereof were used for the following experiments.

EXAMPLE 5

Quality Control of the Fraction of *C. officinale*, AS44-C-2

AS44-C-2 was applied to HPLC (Waters) equipped with Waters 996 photodiode array UV detector. An analytical reversed phase column (Waters Xterra C18; 5 µm, 150×3.9 mm) was used for separations. The mobile phase consisted of methanol and water using a gradient elution of 30%-70% methanol at 50 min. The flow rate was 0.8 ml/min.

Figure 2:
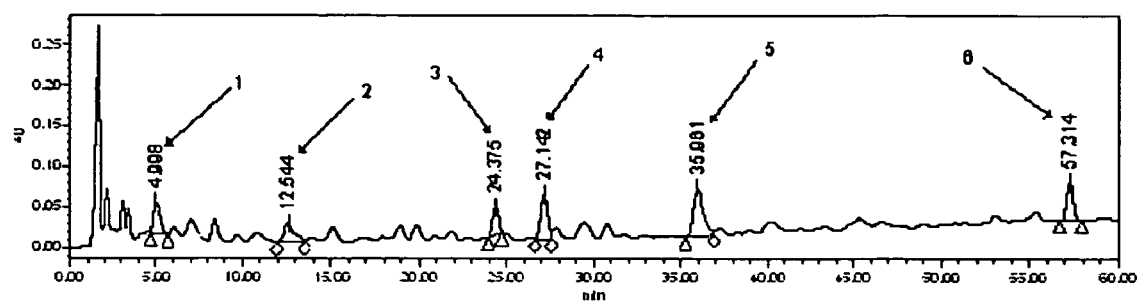
FIG. 2 is a HPLC chromatogram of fraction of *C. officinale* (AS44-C-2).

The HPLC chromatogram of AS44-C-2 fraction of *C. officinale* is shown in FIG. 2.

Total content of active compounds, peak 5 and peak 6 was 41% of AS44-C-2 fraction.

| Peak | Retention time (min) | % | Identification |
|---|---|---|---|
| 5 | 35.961 | 27 | 3-butyl-7-hydroxyphthalide |
| 6 | 57.314 | 14 | falcarindiol |

REFERENCE EXAMPLE 1

Isolation and Culture of HUVEC

Human umbilical vein endothelial cells (HUVECs) were isolated from freshly obtained cords after cesarean section according to Grants' method (Grants D S et al., *Cell*, 58, pp 923-943, 1989). The isolated HUVECs were grown in culture media comprising M-199 (Gibco BRL, 31100-035), 10% FBS, 50 µg/ml ECGS (Endothelial cell growth supplement, Sigma E2795), and 50 µg/ml heparin (Sigma H3149).

HUVECs were identified by immunocytochemical staining with anti-Factor VIII antibody (DAKO, Code No. M0616) (Vaeln G. et al., *Free Radic. Biol. Med.*, 26, pp 1480-1488, 1999; Rhim J S. et al., *Carcinogenesis*, 19, pp 673-681, 1998).

EXPERIMENTAL EXAMPLE 1

Inhibitory Effect of the Extract of *C. officinale* and the Fraction Thereof on Angiogenesis The effect of the extract of *C. officinale* and the fraction thereof on angiogenesis was investigated in vitro with HUVEC tube formation inhibition assay.

1-1. HUVEC Tube Formation Inhibition Assay

HUVECs isolated in REFERENCE EXAMPLE 1 were cultured within passage 5, and then were divided into 20,000 to 50,000 cells per well of 48 well plate coated with, Matrigel (BD Biosciences, Bedford, Mass.). Crude extracts, non-polar solvent extracts, or fractions of *C. officinale* of EXAMPLES 1 to 4 were added to the above HUVEC culture well at the concentration of 50 µg/ml, respectively, and DMSO was added as a control. They were grown with culture media of the above REFERENCE EXAMPLE 1.

After HUVECs were further incubated at 37° C. for 18 hours, tube formation was observed using microscope. The results were summarized in TABLES 1 and 2 (−: no inhibition of tube formation, +/− rare inhibition of tube formation, +: light inhibition of tube formation and slight tube cleavage, ++: significant inhibition of tube formation and heavy tube cleavage, +++: no tube formation).

Figure 3:
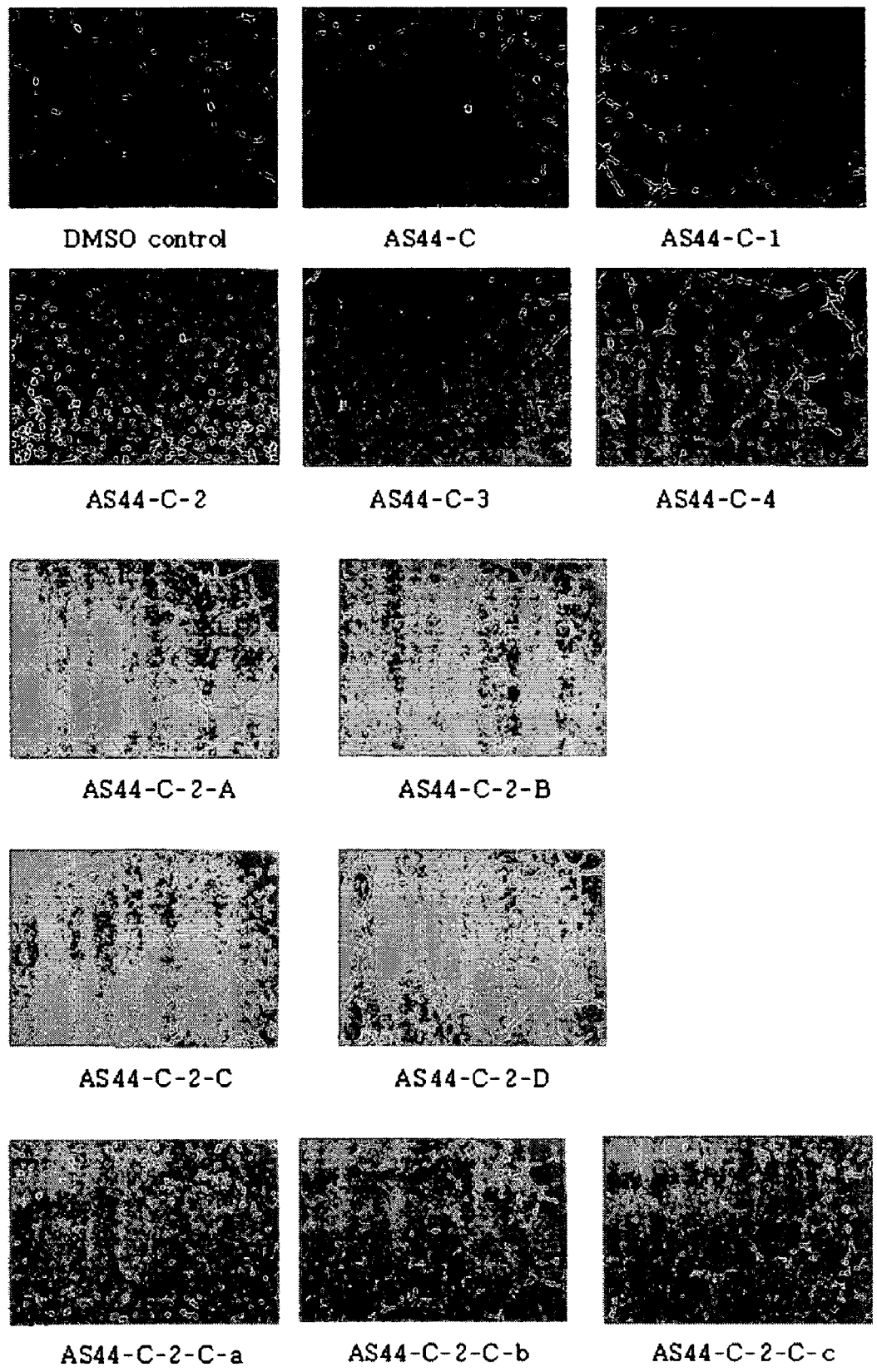
FIG. 3 is a photograph showing HUVEC tube formation inhibition by the extract of *C. officinale* and the fraction thereof.

As shown in TABLE 1, chloroform extract of *C. officinale* (AS44-C) strongly inhibited tube formation. Inhibitory effects of fractions obtained from AS44-C, which were mentioned in EXAMPLE 4, on tube formation were investigated. The fractions of *C. officinale*, AS44-C-2-C, AS44-C-2-C, AS44-C-2-C-b, AS44-C-2-C-b-III, AS44-C-2-D, AS44-C-2-D, AS44-C-2-D-b, and AS44-C-2-D-b-IV strongly inhibited HUVEC tube formation. The results were summarized in TABLE 2 and FIG. 3.

TABLE 1

| Sample | Tube formation inhibition |
|---|---|
| AS44-TW | + |
| AS44-M | + |
| AS44-H | +/− |
| AS44-C | ++ |
| AS44-B | +/− |
| AS44-W | +/− |

TABLE 2

| Sample | Tube formation inhibition |
|---|---|
| AS44-C | + |
| AS44-C-1 | + |
| AS44-C-2 | +++ |
| AS44-C-3 | + |
| AS44-C-4 | + |
| AS44-C-2-A | − |
| AS44-C-2-B | + |
| AS44-C-2-C | +++ |
| AS44-C-2-D | +++ |
| AS44-C-2-E | + |
| AS44-C-2-C-a | − |
| AS44-C-2-C-b | +++ |
| AS44-C-2-C-c | + |
| AS44-C-2-C-d | − |
| AS44-C-2-D-a | − |
| AS44-C-2-D-b | +++ |
| AS44-C-2-D-c | + |
| AS44-C-2-C-b-I | − |
| AS44-C-2-C-b-II | + |
| AS44-C-2-C-b-III | +++ |
| AS44-C-2-C-b-IV | + |
| AS44-C-2-D-b-I | + |
| AS44-C-2-D-b-II | + |
| AS44-C-2-D-b-III | + |
| AS44-C-2-D-b-IV | +++ |
| AS44-C-2-D-b-V | − |

EXPERIMENTAL EXAMPLE 2

Cytotoxicity Assay 2-1. HUVEC Cytotoxicity Assay

Toxic effects of fractions of *C. officinale*, which showed inhibitory effects on HUVEC tube formation, were investigated by cytotoxicity assay against HUVECs mentioned in REFERENCE EXAMPLE 1.

In detail, HUVECs were divided into 5,000 cells per well of 96 well plate, and then fractions of *C. officinale* were added into each well. After one day, the viability of HUVECs was measured by cell proliferation kit II (Roche, Cat. No. 1465015, XTT: 2,3-bis-(2-methoxy-4-nitro-5-sulfophenyl)-2H-tetrazolium-5-carboxanilide disodium salt).

TABLE 3 shows toxic effects of chloroform extract of *C. officinale* and a fraction thereof on HUVEC. 73% of HUVECs were viable at effective concentration of chloroform extract of *C. officinale*.

TABLE 3

| | Viability (%) | |
|---|---|---|
| Sample | 50 µg/ml | 5 µg/ml |
| AS44-C | 95.0 | 119.4 |
| AS44-C-2 | 73.2 | 124.7 |

EXPERIMENTAL EXAMPLE 3

Inhibitory Effects of Crude Extract of *C. officinale* (AS44-TW) on Angiogenesis Using Mouse-Matrigel Model Effects of crude extract of *C. officinale* (AS44-TW) on angiogenesis were investigated in vivo using mouse-Matrigel model.

0.4 ml portion of Matrigel mixed with 50 ng/ml of basic fibroblast growth factor (bFGF) and 50 units/ml of heparin was implanted into C57BL/6 female mice of 6 to 8 week old SLC, Inc. Japan) by subcutaneous injection. To each mouse, 1 mg of AS44-TW was orally administered twice a day for four days. After 5 days, the Matrigel was recovered from excised skin of each mouse and the amount of hemoglobin in the Matrigel was measured by Drabkin kit (Sigma Chemical C., St. Louise, Mich., U.S.A., Cat. No. 525), a reagent for determination of total hemoglobin in blood.

For the control group, water was administered as the same method mentioned above, and then the amount of hemoglobin in the Matrigel was also measured.

Figure 4:
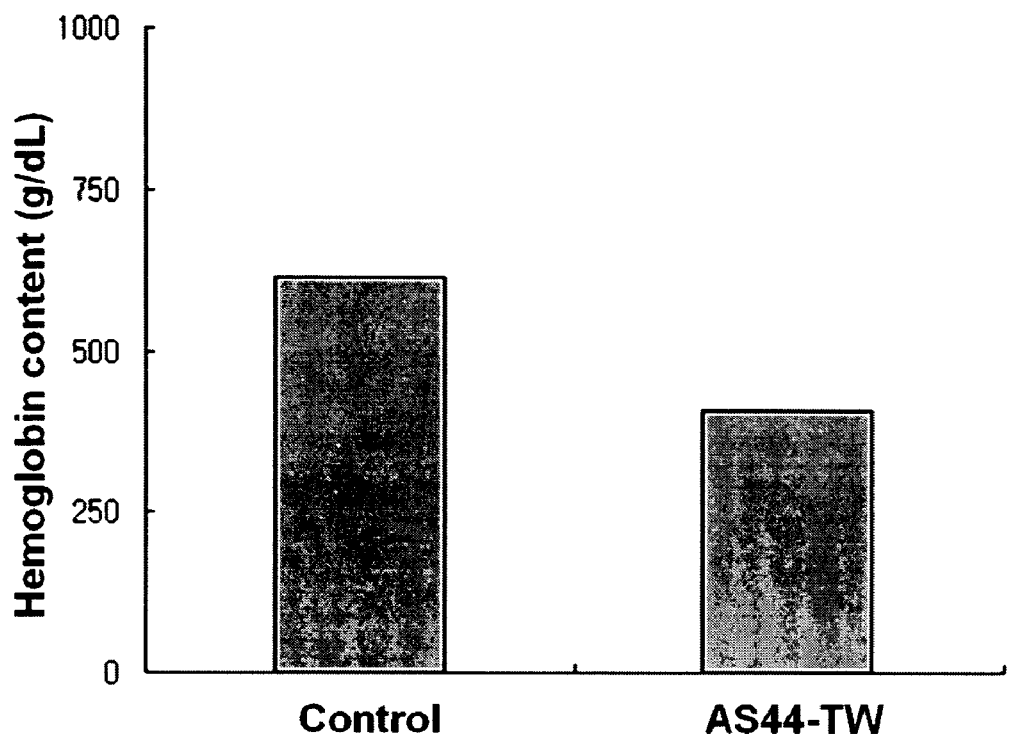
FIG. 4 is a graph of effect of crude extract of *C. officinale* (AS44-TW) on angiogenesis in animal model.

As shown in TABLE 4 and FIG. 4, the average of total hemoglobin levels in the Matrigel from AS44-TW-treated group were below that of the control group, and AS44-TW inhibited angiogenesis by about 33% when it was administered.

TABLE 4

|         | Hemoglobin content (g/dL) | Inhibition (%) |
|---------|---------------------------|----------------|
| Control | 613                       | 0              |
| AS44-TW | 407                       | 33             |

EXPERIMENTAL EXAMPLE 4

Inhibitory Effects of AS44-C-2 on Angiogenesis Using Mouse-Matrigel Model

Figure 5:
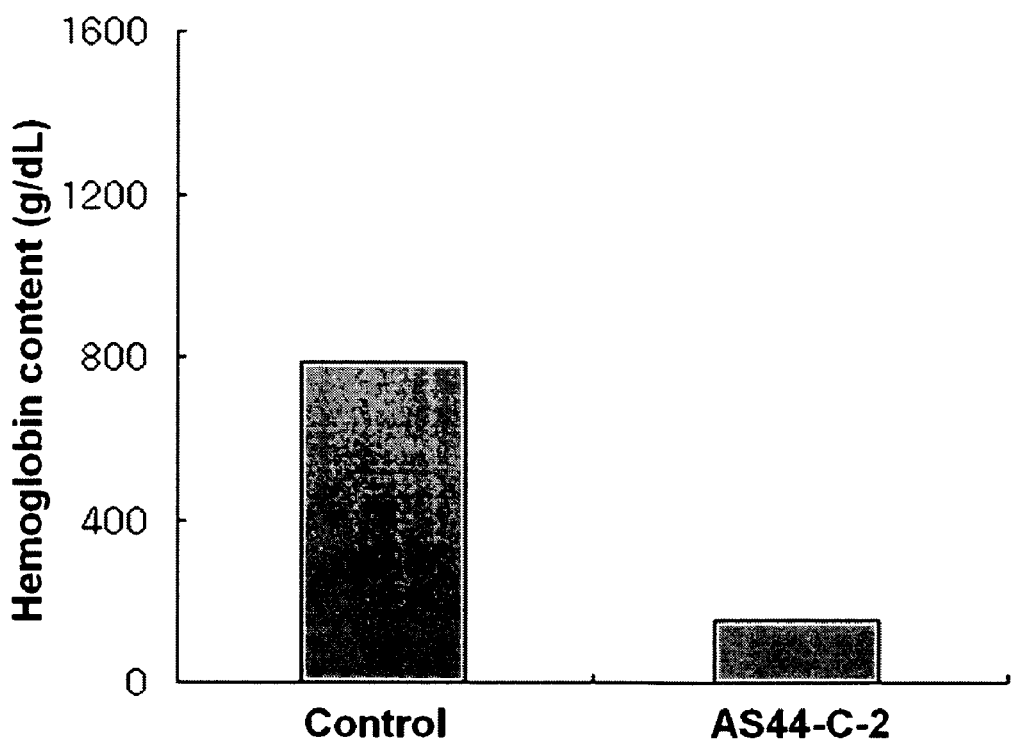
FIG. 5 is a graph of effect of fraction of *C. officinale* (AS44-C-2) on angiogenesis in animal model.

As the same method of the above EXPERIMENTAL EXAMPLE 3, 0.4 ml portion of Matrigel mixed with 50 ng/ml of bFGF and 50 units/ml of heparin was implanted into C57BL/6 female mice by subcutaneous injection. To each mouse, 1.5 mg of AS44-C-2 was orally administered twice a day for four days. AS44-C-2 inhibited angiogenesis by about 80% (TABLE 5 and FIG. 5).

TABLE 5

|          | Hemoglobin content (g/dL) | Inhibition (%) |
|----------|---------------------------|----------------|
| Control  | 788                       | 0              |
| AS44-C-2 | 157                       | 80             |

EXPERIMENTAL EXAMPLE 5

Inhibitory Effects of Fraction of *C. officinale* (AS44-C-2) on Corneal Neovascularization Inhibitory effects of fraction of *C. officinale* (AS44-C-2) on angiogenesis were investigated using corneal neovascularization induced by vascular endothelial growth factor (VEGF). Corneal neovascularization was induced in Sprague-Dawly rats by a standard micropocket assay using pellets with 250 ng VEGF and various doses of AS44-C-2 (0, 0.05, 0.5, 1 µg).

The sustained release polymer pellets were prepared as described earlier (Kenyon B M et al., *Invest. Ophthalmol Vis. Sci.*, 37, pp 1625-1632, 1996). Pellets were made using the slow release polymer Hydron (polyhydroxyehtylmethacrylate, polyHEMA) and contained VEGF and different doses of AS44-C-2. Each pellet contained 250 ng of 0, 0.05, 0.5, or 0.1 µg of AS44-C-2.

To stimulate a reliable and reproducible neovascular response, the technique of modified rat corneal micropocket assay was used as described earlier (Kenyon B M et al., *Invest. Ophthalmol Vis. Sci.*, 37, pp 1625-1632, 1996; Li W W et al., *Invest. Ophthalmol Vis. Sci.*, 32, pp 2906-2911, 1991). The eyes were proptosed by grasping the nasal conjuctiva around the limbus using tooth forceps, and the entrance of corneal intrastromal lamellar pocket (approximately 50% deep, 1 mm wide) was made along the limbus with a clear-cut blade. Then, intrastromal pocket was extended 1.5-2 mm away from the entrance with an iris spatula. The pellet was grasped by smooth forceps and implanted into the corneal stroma pocket in each eye. Topical 0.3% ofloxacin ointment (Tarivid, Santen, Japan) was applied for 3 days to prevent infection.

Eyes in this study were randomly divided into four groups. Each eye in the control group (n=21) was implanted with the pellet containing VEGF without AS44-C-2. Group A (n=16) was implanted with the pellet containing VEGF and 0.5 µg of AS44-C-2, group B (n=21) with the pellet containing VEGF and 0.1 µg of AS44-C-2 and group C (n=11) with the pellet containing VEGF and 0.05 µg of AS44-C-2.

5-1. Quantification of Corneal Neovascularization

The photographs were obtained at 1 week after pellet implantation. Actual values of width, length, and number of new vessels were assigned to the designated score. The following table shows the scoring standard for evaluating the actual values of each parameter. Finally, corneal neovascularization score was acquired by multiplying each parameter.

| Width (mm) | Length (mm) | Number of new vessels | Score |
|------------|-------------|-----------------------|-------|
| -2.0       | -1.5        | -10                   | 1     |
| 2.0-3.0    | 1.5-2.0     | 10-15                 | 2     |
| 3.0-4.0    | 2.0-2.5     | 15-20                 | 3     |
| 4.0-       | 2.5-        | 20-                   | 4     |

Figure 6:
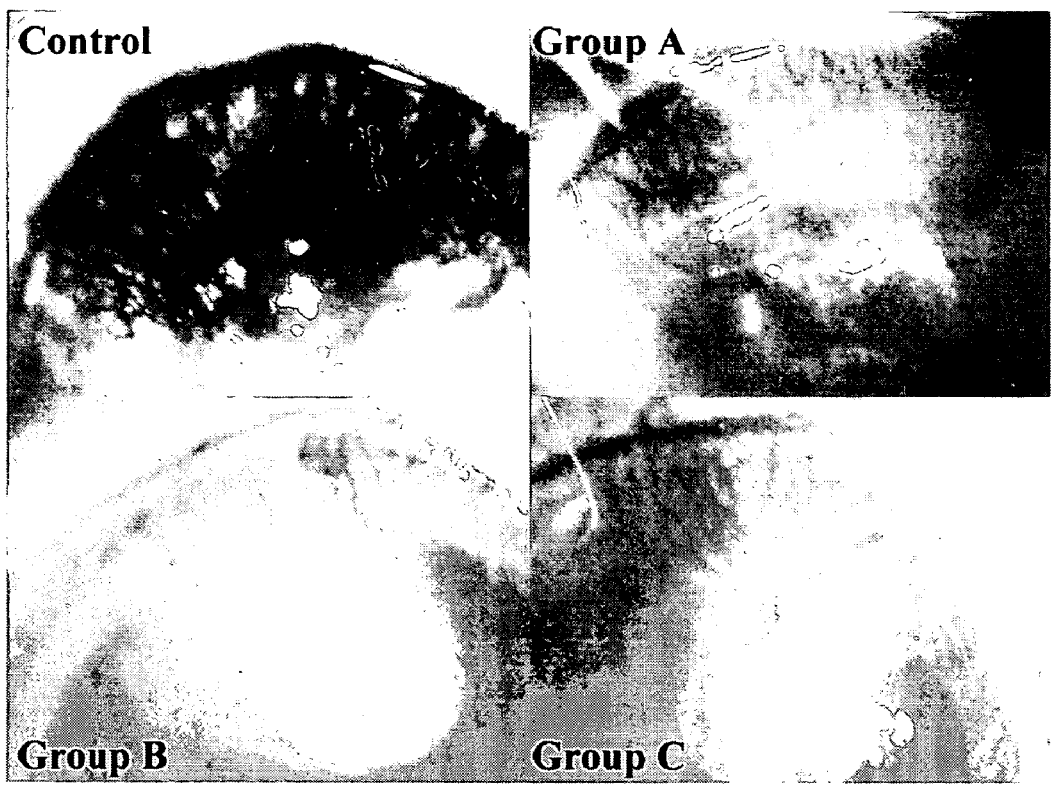
FIG. 6 is a photograph showing corneal neovascularization inhibition by fraction of *C. officinale* (AS44-C-2).
Figure 7:
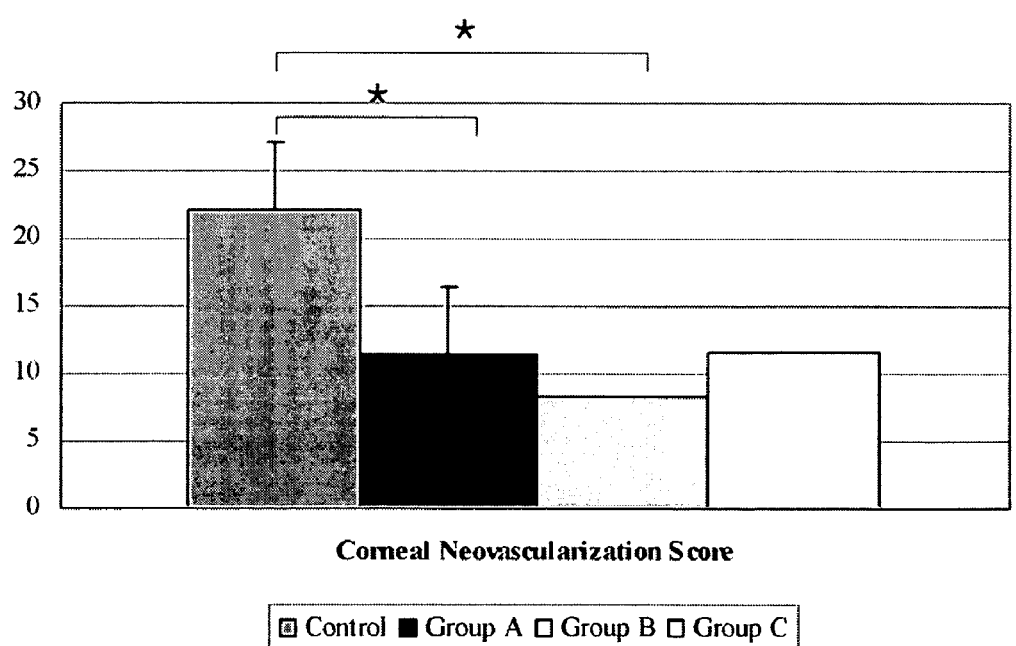
FIG. 7 is a graph of effect of fraction of *C. officinale* (AS44-C-2) on corneal neovascularization score.

Groups treated with VEGF pellets with all doses of AS44-C-2 had significantly less corneal neovascularization score than did control (FIG. 6 and FIG. 7). There were no significant differences among eyes implanted with different doses of AS44-C-2 in all the parameters and the corneal neovascularization score.

5-2. Immunohistochemical Examination

Figure 8:
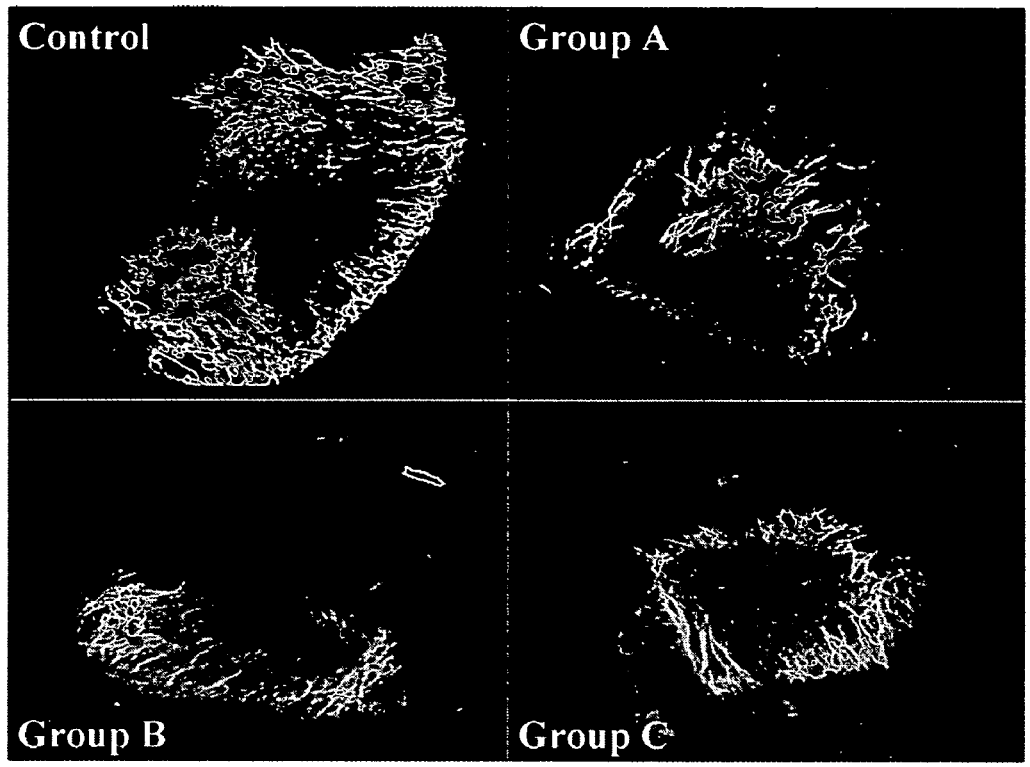
FIG. 8 is a photograph of FITC-coupled anti-CD31 stained corneal flatmounts of control group and groups treated with fraction of *C. officinale* (AS44-C-2).

Reduced neovascularization of AS44-C-2 treated groups was confirmed by immunohistochemical staining with FITC-coupled anti-CD31 antibody (FIG. 8).

Immunohistochemical staining for vascular endothelial cells was performed on corneal flatmounts. Fresh corneas were dissected, rinsed in PBS for 30 min, fixed in 100% acetone for 20 min and blocked with 0.3% Triton-X in PBS for 30 min at room temperature. After the corneas were washed in PBS, nonspecific binding was blocked with 0.1 M PBS, 2% albumin for 1 hour at room temperature. Incubation with FITC-coupled monoclonal anti-mouse CD31 antibody at a concentration of 1:300 in 0.1 M PBS, 2% albumin at 4° C. for 2 days was followed by subsequent washes in PBS at room temperature. Corneas were mounted with an anti-fading agent and visualized with a fluorescence microscope (Leica, Wetzler, Germany).

5-3. Histological Examination

At 1 week after pellet implantation, the rats were sacrificed with an overdose of Pentothal and their eyes were enucleated. Corneas were excised and fixed in paraformaldehyde for 24 hours. Then, corneas were fixed in paraffin block overnight, cut into 5 μm section and prepared for hematoxylin and eosin (H&E) staining.

Figure 9:
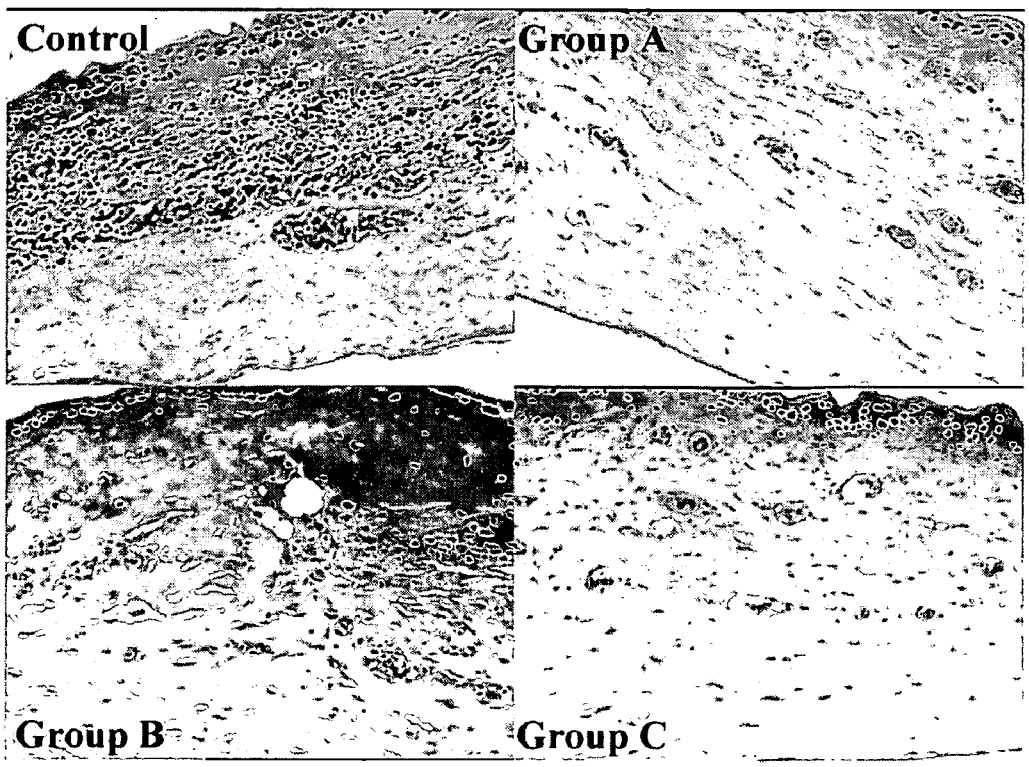
FIG. 9 is a photograph of H&E stained cornea of control group and treated groups treated with fraction of *C. officinale* (AS44-C-2).

Histological analysis showed significant inhibition of corneal neovascularization and quiescent inflammatory response with less leukocyte aggregation in treated groups (FIG. 9). Inflammatory responses with infiltration of PMNs, macrophages and other inflammatory cells, which are accompanied by new vascular lumen formation, were found in all groups. However, in eyes implanted with pellets containing AS44-C-2, less severe inflammatory response and reduced number of new vessels were found than in control eyes.

Extracts and fractions of the present invention may be administered by the following formulations. However, these examples are shown only for better understanding the present invention without limiting its scope.

FORMULATION EXAMPLE 1

Preparation of Pill

Pills containing fractions of *C. officinale* were prepared by mixing the following ingredients and manufacturing 0.3 cm-diameter pills as conventional method.

| | |
|---|---|
| Fractions of *C. officinale* of EXAMPLE 3 | 120 mg |
| Cornstarch | 100 mg |
| Distilled water | q.s. |

FORMULATION EXAMPLE 2

Preparation of Tablet

Tablets containing fractions of *C. officinale* were prepared by mixing the following ingredients and tableting as conventional method.

| | |
|---|---|
| Fractions of *C. officinale* of EXAMPLE 3 | 200 mg |
| Lactose | 100 mg |
| Starch | 100 mg |
| Magnesium stearate | q.s. |

FORMULATION EXAMPLE 3

Preparation of Capsule

Capsules containing fractions of *C. officinale* were prepared by mixing the following ingredients and filling in gelatin capsules as conventional method.

| | |
|---|---|
| Fractions of *C. officinale* of EXAMPLE 3 | 100 mg |
| Lactose | 100 mg |
| Starch | 100 mg |
| Talc | 2 mg |
| Magnesium stearate | q.s. |

FORMULATION EXAMPLE 4

Preparation of Liquid Medicine

Adequate amount of water was added to make the solution 1000 ml. Liquid medicine containing crude extract of *C. officinale* was prepared by mixing the following ingredients, filling into brown bottle, and sterilizing as conventional method.

| | |
|---|---|
| Crude extract of *C. officinale* of EXAMPLE 1 | 1000 mg |
| Sugar | 20 g |
| Isomerized sugar | 20 g |
| Lemon flavor | q.s. |

FORMULATION EXAMPLE 5

Preparation of Nutraceutical Food

The following composition of vitamin and mineral mixtures was comprised of adequate ingredients for nutraceutical food as a desirable example. However, it is not limited and their composition can be modified at discretion. Nutraceutical food containing crude extract of *C. officinale* was prepared by mixing the following ingredients and granulating as conventional method.

| | |
|---|---|
| Crude extract of *C. officinale* of EXAMPLE 2 | 1000 mg |
| Vitamin mixture | q.s. |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Inorganic mixture | q.s. |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

FORMULATION EXAMPLE 6

Preparation of Nutraceutical Beverage

Nutraceutical beverage containing crude extract of *C. officinale* was prepared by mixing the following ingredients, heating at 85° C. for 1 hour, filtrating, filling into 2 liter bottle, sealing, sterilizing, and keeping in cold storage as conventional method.

The following composition was comprised of adequate ingredients for favorite beverage as a desirable example. However, it is not limited and their composition can be modified at discretion.

| | |
|---|---|
| Crude extract of *C. officinale* of EXAMPLE 1 | 1000 mg |
| Citrate | 1000 mg |
| Oligosaccharide | 100 g |
| Concentrated extract of plum | 2 g |
| Taurine | 1 g |
| Distilled water | q.s. |

INDUSTRIAL APPLICABILITY

As above-mentioned, the extract and fraction of the present invention containing the active ingredients from *C. officinale* inhibit angiogenesis. Based on the results, the extract of *C. officinale* and the fraction thereof can be used as a new composition for the prevention or treatment of angiogenesis-related disease, such as arthritis, diabetic retinopathy, psoriasis, cancer, and so on.

The invention claimed is:

1. A method of treating an ophthalmologic disease associated with angiogenesis in a subject having said disease comprising administering an isolated compound selected from the group consisiting of 3-butyl-7-hydroxyphthalide, falcarindiol, vanillin, coniferyl ferulate, and any combination thereof to said subject.

2. The method according to claim 1, wherein the ophthalmologic disease is corneal neovascularization.

3. The method according to claim 1, wherein the ophthalmologic disease is neovascularization after cornea implantation, neovascular glaucoma, diabetic retinopathy, angiogenic corneal disease, macular degeneration, pterygium, retinal degeneration, retolental fibroplasias, or granular conjunctivitis. disease is psoriasis, telangiectasis, pyogenic granuloma, seborrheic dermatitis or acne.

4. The method of claim 1, wherein said compound is isolated comprising use of a solvent selected from the group consisiting of hexane, chloroform, methlylene chloride, and ethyl acetate.

* * * * *